US006605031B1

(12) United States Patent
Mourtada et al.

(10) Patent No.: US 6,605,031 B1
(45) Date of Patent: Aug. 12, 2003

(54) STEPPED CENTERING BALLOON FOR OPTIMAL RADIATION DELIVERY

(75) Inventors: Firas Mourtada, Houston, TX (US); Eric D. Peterson, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/505,340

(22) Filed: Feb. 16, 2000

Related U.S. Application Data

(60) Provisional application No. 60/155,929, filed on Sep. 22, 1999.

(51) Int. Cl.[7] .............................................. A61M 36/04
(52) U.S. Cl. .......................................................... 600/3
(58) Field of Search .................. 600/1–8; 606/191–192, 606/194

(56) References Cited

U.S. PATENT DOCUMENTS

| | | |
|---|---|---|
| 3,560,291 A | 2/1971 | Foglia et al. |
| 3,769,117 A | 10/1973 | Bowen et al. |
| 3,974,016 A | 8/1976 | Bondybey et al. |
| 4,069,080 A | 1/1978 | Osborne |
| 4,156,626 A | 5/1979 | Souder |
| 4,195,637 A | 4/1980 | Gruntzig et al. |

(List continued on next page.)

FOREIGN PATENT DOCUMENTS

| | | |
|---|---|---|
| EP | 0633041 A1 | 1/1995 |
| EP | 0688580 A1 | 12/1995 |
| EP | 0801961 A2 | 10/1997 |
| EP | 0829271 A2 | 3/1998 |
| EP | 0865803 A2 | 9/1998 |

(List continued on next page.)

OTHER PUBLICATIONS

–Stuart Lindsay et al., "Aortic Arteriosclerosis in The Dog After Localized Aortic X–Irradiation", *Circulation Research*, vol. X, pp 51–60, Jan. 1962.
–Meyer Friedman et al., "The Antiatherogenic Effect of Iridium[192] Upon the Cholesterol–Fed Rabbit", *Journal of Clinical Investigation*, vol. 43, No. 2, pp 185–192, 1964.
–Meyer Friedman et al., "Effect of Iridium[192] Radiation on Thromboatherosclerotic Plaque in the Rabbit Aorta", *Arch Path*, vol. 80, pp 285–290, Sep. 1965.
–Paul Jack Hoopes, D.V.M., Ph.D. et al., "Intraoperative Irradiation of the Canine Abdominal Aorta and Vena Cava", *Int. J. Radiation Oncology Biol. Phys.*, vol. 13, pp. 715–722, May 1987.
–John T. Dawson, Jr. M.D., "Theoretic Considerations Regarding Low–Dose Radiation Therapy", *Texas Heart Institute Journal*, vol. 18, No. 1, pp. 4–7, 1991.

(List continued on next page.)

*Primary Examiner*—Max F. Hindenburg
*Assistant Examiner*—Joseph A. Cadugan
(74) *Attorney, Agent, or Firm*—Blakely, Sokoloff, Taylor & Zafman LLP

(57) ABSTRACT

A stepped centering catheter for delivery of intravascular radiation therapy including a central segment of a first effective diameter and smaller, offset segments of second effective diameters to each side of the central segment. The first effective diameter of the central segment substantially centers a portion of a radiation source within the lumen of a vessel along a therapeutic treatment length. The second effective diameters of the offset segments constrain portions of the radioactive source that extend beyond the therapeutic treatment length within a region having a minimum offset distance from the vessel wall. The first effective diameter of the central segment is gradually tapered to the second effective diameter of the offset segments across first steps. The second effective diameters of the offset segments are gradually tapered to the diameter of the catheter shaft across second steps. The smaller diameter offset segments and tapered change in diameters mitigates further injury to vessel walls located outside the therapeutic treatment length.

32 Claims, 6 Drawing Sheets

U.S. PATENT DOCUMENTS

| | | |
|---|---|---|
| 4,251,305 A | 2/1981 | Becker et al. |
| 4,323,071 A | 4/1982 | Simpson et al. |
| 4,515,651 A | 5/1985 | MacLaughlin et al. |
| 4,537,809 A | 8/1985 | Ang et al. |
| 4,581,017 A | 4/1986 | Sahota |
| 4,661,094 A | 4/1987 | Simpson |
| 4,697,575 A | 10/1987 | Horowitz |
| 4,706,652 A | 11/1987 | Horowitz |
| 4,733,047 A | 3/1988 | Cruickshank et al. |
| 4,744,366 A | 5/1988 | Jang |
| 4,748,982 A | 6/1988 | Horzewski et al. |
| 4,762,130 A | 8/1988 | Forgarty et al. |
| 4,763,671 A | 8/1988 | Goffinet |
| 4,771,777 A | 9/1988 | Horzewski et al. |
| 4,771,778 A | 9/1988 | Mar |
| 4,775,371 A | 10/1988 | Mueller, Jr. |
| 4,790,315 A | 12/1988 | Mueller, Jr. et al. |
| 4,793,351 A | 12/1988 | Landman et al. |
| 4,815,449 A | 3/1989 | Horowitz |
| 4,861,520 A | 8/1989 | Van't Hooft et al. |
| 4,936,823 A | 6/1990 | Colvin et al. |
| 4,940,064 A | 7/1990 | Desai |
| 4,969,863 A | 11/1990 | Van't Hooft et al. |
| 4,976,720 A | 12/1990 | Machold et al. |
| 4,983,167 A | 1/1991 | Sahota |
| 4,994,560 A | 2/1991 | Kruper, Jr. et al. |
| 4,998,917 A | 3/1991 | Gaiser et al. |
| 5,002,560 A | 3/1991 | Machold et al. |
| 5,015,230 A | 5/1991 | Martin et al. |
| 5,019,042 A | 5/1991 | Sahota |
| 5,032,113 A | 7/1991 | Burns |
| 5,034,001 A | 7/1991 | Garrison et al. |
| 5,040,543 A | 8/1991 | Badera et al. |
| 5,046,503 A | 9/1991 | Schneiderman |
| 5,059,166 A | 10/1991 | Fischell et al. |
| 5,061,273 A | 10/1991 | Yock |
| 5,084,002 A | 1/1992 | Liprie |
| 5,087,246 A | 2/1992 | Smith |
| 5,100,429 A | 3/1992 | Sinofsky et al. |
| 5,133,956 A | 7/1992 | Garlich et al. |
| 5,137,513 A | 8/1992 | McInnes et al. |
| 5,151,149 A | 9/1992 | Swartz |
| 5,176,617 A | 1/1993 | Fischell et al. |
| 5,176,661 A | 1/1993 | Evard et al. |
| 5,180,368 A | 1/1993 | Garrison |
| 5,195,971 A | 3/1993 | Sirhan |
| 5,199,939 A | 4/1993 | Dake et al. |
| 5,213,561 A | 5/1993 | Weinstein et al. |
| 5,226,889 A | 7/1993 | Sheiban |
| 5,242,396 A | 9/1993 | Evard |
| 5,258,419 A | 11/1993 | Rolando et al. |
| 5,263,963 A | 11/1993 | Garrison et al. |
| 5,267,960 A | 12/1993 | Hayman et al. |
| 5,273,738 A | 12/1993 | Matthews et al. |
| 5,279,562 A | 1/1994 | Sirhan et al. |
| 5,282,781 A | 2/1994 | Liprie |
| 5,295,959 A | 3/1994 | Gurbel et al. |
| 5,295,960 A | 3/1994 | Aliahmad et al. |
| 5,295,995 A | 3/1994 | Kleiman |
| 5,300,281 A | 4/1994 | McMillan et al. |
| 5,302,168 A | 4/1994 | Hess |
| 5,306,246 A | 4/1994 | Sahatjian et al. |
| 5,308,356 A * | 5/1994 | Blackshear, Jr. et al. ... 606/194 |
| 5,320,824 A | 6/1994 | Brodack et al. |
| 5,334,154 A | 8/1994 | Samson et al. |
| 5,336,518 A | 8/1994 | Narayanan et al. |
| 5,350,361 A | 9/1994 | Tsukashima et al. |
| 5,352,199 A | 10/1994 | Tower |
| 5,354,257 A | 10/1994 | Roubin et al. |
| 5,380,747 A | 1/1995 | Medford et al. |
| 5,395,333 A | 3/1995 | Brill |
| 5,405,622 A | 4/1995 | Vernice et al. |
| 5,409,495 A | 4/1995 | Osborn |
| 5,411,466 A | 5/1995 | Hess |
| 5,415,664 A | 5/1995 | Pinchuk |
| 5,425,710 A | 6/1995 | Khair et al. |
| 5,441,516 A | 8/1995 | Wang et al. |
| 5,447,497 A | 9/1995 | Sogard et al. |
| 5,456,667 A | 10/1995 | Ham et al. |
| 5,458,572 A | 10/1995 | Campbell et al. |
| 5,484,384 A | 1/1996 | Fearnot |
| 5,498,227 A | 3/1996 | Mawad |
| 5,501,667 A | 3/1996 | Verduin, Jr. |
| 5,501,759 A | 3/1996 | Forman |
| 5,503,613 A | 4/1996 | Weinberger |
| 5,503,614 A | 4/1996 | Liprie |
| 5,507,301 A | 4/1996 | Wasicek et al. |
| 5,507,769 A | 4/1996 | Marin et al. |
| 5,516,336 A | 5/1996 | McInnes et al. |
| 5,540,659 A | 7/1996 | Teirstein |
| 5,542,925 A | 8/1996 | Orth |
| 5,549,552 A | 8/1996 | Peters et al. |
| 5,573,508 A | 11/1996 | Thornton |
| 5,573,509 A | 11/1996 | Thornton |
| 5,599,306 A | 2/1997 | Klein et al. |
| 5,616,114 A | 4/1997 | Thornton et al. |
| 5,618,266 A | 4/1997 | Liprie |
| 5,643,171 A * | 7/1997 | Bradshaw et al. ............ 600/1 |
| 5,653,691 A | 8/1997 | Rupp et al. |
| 5,658,311 A | 8/1997 | Baden |
| 5,674,177 A | 10/1997 | Hehrlein et al. |
| 5,683,345 A | 11/1997 | Waksman et al. |
| 5,688,486 A | 11/1997 | Watson et al. |
| 5,707,332 A | 1/1998 | Weinberger |
| 5,730,698 A | 3/1998 | Fischell et al. |
| 5,738,901 A | 4/1998 | Wang et al. |
| 5,749,852 A | 5/1998 | Schwab et al. |
| 5,762,906 A | 6/1998 | Creighton |
| 5,766,192 A | 6/1998 | Zacca |
| 5,782,740 A * | 7/1998 | Schneiderman ................ 600/1 |
| 5,782,742 A * | 7/1998 | Crocker et al. ................ 600/3 |
| 5,797,869 A | 8/1998 | Martin et al. |
| 5,797,948 A * | 8/1998 | Dunham ..................... 606/194 |
| 5,826,588 A | 10/1998 | Forman |
| 5,836,965 A | 11/1998 | Jendersee et al. |
| 5,840,064 A | 11/1998 | Liprie |
| 5,840,067 A | 11/1998 | Berguer et al. |
| 5,851,171 A | 12/1998 | Gasson |
| 5,855,546 A * | 1/1999 | Hastings et al. ................ 600/3 |
| 5,863,284 A * | 1/1999 | Klein ........................... 600/3 |
| 5,863,285 A * | 1/1999 | Coletti ......................... 600/3 |
| 5,871,436 A | 2/1999 | Eury |
| 5,882,290 A | 3/1999 | Kume |
| 5,882,291 A * | 3/1999 | Bradshaw et al. ............ 600/3 |
| 5,899,882 A | 5/1999 | Waksman et al. |
| 5,910,101 A * | 6/1999 | Andrews et al. ................ 600/3 |
| 5,938,582 A | 8/1999 | Ciamacco, Jr. et al. |
| 5,947,924 A | 9/1999 | Liprie |
| 5,951,458 A | 9/1999 | Hastings et al. |
| 5,954,741 A | 9/1999 | Fox |
| 5,961,765 A | 10/1999 | Kastenhofer |
| 5,964,730 A | 10/1999 | Williams et al. |
| 5,976,106 A | 11/1999 | Verin et al. |
| 5,984,963 A | 11/1999 | Ryan et al. |
| 6,074,338 A * | 6/2000 | Popowski et al. ............. 600/3 |
| 6,074,339 A * | 6/2000 | Gambale et al. ................ 600/3 |
| 6,099,499 A * | 8/2000 | Ciamacco, Jr. ............. 604/103 |
| 6,149,574 A * | 11/2000 | Trauthen et al. ................ 600/3 |
| 6,183,410 B1 * | 2/2001 | Jacobsen et al. ................ 600/3 |
| 6,213,976 B1 * | 4/2001 | Trerotola .................... 604/104 |

FOREIGN PATENT DOCUMENTS

| EP | 0879614 A1 | 11/1998 |
|---|---|---|
| WO | WO 92/17236 | 10/1992 |
| WO | WO 93/04735 | 3/1993 |
| WO | WO 94/25106 | 11/1994 |
| WO | WO 95/19807 | 7/1995 |
| WO | WO 95/26681 | 10/1995 |
| WO | WO 96/06654 | 3/1996 |
| WO | WO 96/10436 | 4/1996 |
| WO | WO 96/14898 | 5/1996 |
| WO | WO 96/19255 | 6/1996 |
| WO | WO 97/07740 | 3/1997 |
| WO | WO 97/37715 | 10/1997 |
| WO | WO 97/40889 | 11/1997 |
| WO | WO 98/01182 | 1/1998 |
| WO | WO 98/01183 | 1/1998 |
| WO | WO 98/01184 | 1/1998 |
| WO | WO 98/01185 | 1/1998 |
| WO | WO 98/39052 | 9/1998 |
| WO | WO 99/20324 | 4/1999 |
| WO | WO 99/40962 | 8/1999 |
| WO | WO 99/40971 | 8/1999 |
| WO | WO 99/40972 | 8/1999 |
| WO | WO 99/40973 | 8/1999 |
| WO | WO 99/40974 | 8/1999 |

OTHER PUBLICATIONS

–Robert S. Schwartz, M.D. et al. "Effect of External Beam Irradiation on Neointimal Hyperplasia After Experimental Coronary Artery Injury", *JACC*, vol. 19, No. 5, pp. 1106–1113, Apr. 1992.
–Joseph G. Wiedermann, M.D. et al.,"Intracoronary Irradiation Markedly Reduces Restenosis After Balloon Angioplasty in a Porcine Model", *JACC*, vol. 23, No. 6, pp. 1491–1498, May 1994.
Tim A. Fischell, M.D. et al., "Low–Dose B–Particle Emission from 'Stent' Wire Results in Complete, Localized Inhibition of Smooth Muscle Cell Prolifertion", *Circulation*, vol. 90, No. 6, pp. 2956–2963, Dec. 1994.
Maria G. M. Hunink, M.D. et al., "Risks and Benefits of Femoropopliteal Percutaneous Balloon Angiplasty", *Journal of Vascular Surgery*, vol. 17, No. 1, pp. 183–194, Jan. 1993.
–Ron Waksman M.D. et al., "Endovascular Low–Dose Irradiation Inhibits Neointima Formation After Coronary Artery Balloon Injury in Swine", *Circulation*, vol. 91, No. 5, pp. 1533–1539, Mar. 1, 1995.
–Z. Weshler et al., "Inhibition by Irradiation of Smooth Muscle Cell Proliferation in the De–Endothelialized Rat Aorta", *Frontiers in Radiation Biology*, pp. 133–138, Oct. 1988.
–C. Hehrlein et al. "Radioactive Stents", *Discoveries in Radiation for Restenosis*, Abstract 22, pp. 63–64, Jan. 1996.
–Tim. A. Fischell, M.D. et al., "A Beta–Particle Emitting Radioisotope Stent for The Prevention of Restenosis," *Discoveries in Radiation for Restenosis*, Abstract 23, p. 65, Jan. 1996.
–Alexander N. Ll et al., "A Novel Brachyehtapy Source for Treatment of Coronary Artery Restenosis," *Discoveries in Radiation for Restenosis*, Abstract 24, pp. 67–72, Jan. 1996.
–Ron Waksman, M.D., "Catheter–Based Radiation In Stented Arteries", *Discoveries in Radiation for Restenosis*, Abstract 25, pp. 73–74, Jan. 1996.
–Louis G. Martin, M.D., "Radiation for Peripheral Applications: Technical Aspects," *Discoveries in Radiation for Restenosis*, Abstract 27, pp. 81–82, Jan. 1996.

–Alan B. Lumsden, M.D. et al, "Restenosis in Peripheral Vascular Disease," *Discoveries in Radiation for Restenosis*, Abstract 28, pp. 83–88, Jan. 1996.
–B. Schopohl et al., "Endovascular Irradiation for Avoidance or Recurrent Stenosis After Stent Implantation in Peripheral Arteries–5 years Follow–up", *Discoveries in Radiation for Restenosis*, Abstract 29, pp. 89–92, Jan. 1996.
–Ron Waksman, M.D., "Radiation in the Peripheral System at Emory," *Discoveries in Radiation for Restenosis*, Abstract 30, pp. 93–94, Jan. 1996.
–Paul S. Teirstein et al., "Catheter–Based Radiation Therapy to Inhibit Restenosis Following Coronary Stenting," *Discoveries in Radiation for Restenosis*, Abstract 31, p. 99, Jan. 1996.
–Spencer B. King III, M.D., "Clinical Restenosis Trials Using Beta Energy Radiation," *Discoveries in Radiation for Restenosis*, Abstract 32, pp. 101–102, Jan. 1996.
–Philip Urban, M.D. et al., "Endovascular Irradiation with 90Y Wire", *Discoveries in Radiation for Restenosis*, Abstract 33, pp. 103–104, Jan. 1996.
–Jose A. Condado, et al., "Late Follow–up After Percutaneous Transluminal Coronary Angioplasty (PTCA) and Intracoronary Radiation Therapy (ICRT)," *Discoveries in Radiation for Restenosis*, Abstract 34, p. 105, Jan. 1996.
–Thomas D. Weldon, "Catheter Based Beta Radiation System", *Discoveries in Radiation for Restenosis*, Abstract 35, p. 111, Jan. 1996.
–Richard V. Calfee, Ph.D., "High Dose Rate Afterloader System For Endovascular Use–Neocardia", *Discoveries in Radiation for Restenosis*, Abstract 39, pp. 119, Jan. 1996.
–Dr. Edward F. Smith III, "Issues on Handling Radioactive Devices to Prevent Restenosis", , *Discoveries in Radiation for Restenosis*, Abstract 40, pp. 121–122, Jan. 1996.
–Richard E. Kunts, M.D. et al., "Generalized Model of Restenosis After Conventional Balloon Angioplasty, Stenting and Directional Atherectomy", *JACC*, vol. 21, No. 1, pp. 15–25, Jan. 1993.
–Robert S. Schwartz et al., "Differential Neointimal Response to Coronary Artery Injury in Pigs and Dogs", *Arteriosclerosis and Thrombosis*, vol. 14, No. 3, pp. 395–400, Mar. 1994.
–Michael Haude, M.D. et al, "Quantitative Analysis of Elastic Recoil after Balloon Angioplasty and After Intracoronary Implantation of Balloon–Expandable Palmaz–Schatz Stents", *JACC*, vol. 21, No. 1, pp. 26–34, Jan. 1993.
William S. Weintraub M.D. et al., "Can Restenosis After Coronary Angiplasty Be Predicted From Clinical Variables?", *JACC*, vol. 21, No. 1, pp. 6–14, Jan. 1993.
–Tsunekazu Kakuta, M.D. et al., "Differences in Compensatory Vessel Enlargement, Not Intimal Formation, Account for Restenosis After Angioplasty in the Hypercholesterolemic Rabbit Model," *Circulation*, vol. 89, No. 6, pp. 2809–2815, Jun. 1994.
–Christina Unterberg, M.D. et al., "Reduced Acute Thrombus Formation Results in Decreased Neointimal Proliferation After Coronary Angioplasty", *JACC*, vol. 26, No. 7, pp. 1747–1754, Dec. 1995.
Lewis W. Johnson et al., "Review of Radiation Safety in the Cardiac Catheterization Laboratory", *Catheterization and Cardiovascular Diagnosis*, vol. 25, pp. 186–194, 1992.
–Roger W. Byhardt et al., "The Heart and Blood Vessels", *Radiation Oncology Rationale, Technique, Results*, pp. 277–284, Jan. 1996.

–C.G. Soares et al., "Measurement of Radial Dose Distributions Around Small Beta Particle Emitters Using High Resolution Radiochromic Foil Dosimetry", *Nuclear Technology Publishing*, vol. 4, No. 1, pp. 367–372, 1992.

Louis K. Wagner, Ph.D. et al., "Potential Biological Effects Following High X–Ray Dose Intervational Procedures", *Journal of Vascular and Interventional Radiology*, pp. 71–84, Jan.–Feb. 1994.

–Ron Waksman M.D. et al., "Intracoronary Low–Dose B–Irradiation Inhibits Neointima Formation After Coronary Artery Balloon Injury in the Swine Restenosis Model", *Circulation*, vol. 92, No. 10, pp. 3025–3031, Nov. 15, 1995.

–Joseph G. Wiedermann, M.D. et al., "Intracoronary Irradiation Markedly Reduces Neointimal Proliferation After Balloon Angioplasty in Swine: Persistent Benefit at 6–month Follow–up", *JACC* vol. 25, No. 1, pp. 1451–1456, May 1995.

–Dieter Liermann et al., "Prophylactic Endovascular Radiotherapy to Prevent Initmal Hyperplasia After Stent Implantation in Femoropoliteal Arteries", *Cardiovascular and Interventional Radiology*, vol. 17, pp. 12–16, 1994. pg. 14.

–Joseph G. Widermann et al., "Effects of High–Dose Intracoronary Irradiation on Vasomotor Function and Smooth Muscle Histopathology", *Intracoronary Irradiation and Vasomotion*, pp. . H125–H132, 1994.

Keith L. March, M.D. et al., "8–Methoxypsoralen and Longwave Ultraviolet Irradiation Are a Novel Antiproliferative Combination for Vascular Smooth Muscle", *Circulation*, vol. 87, No. 1, pp. 184–191, Jan. 1993.

–Barry T. Katzen, M.D., "Mechanical Approaches to Restenosis in the Peripheral Circulation", Jan. 1996.

–Vitali Verin, M.D., et al., "Intra–Arterial Beta Irradiation Prevents Neointimal Hyperplasia in a Hypercholesterolemic Rabbit Restenosis Model", *Circulation*, vol. 92, No. 8, pp. 2284–2290, Oct. 15, 1995.

–Ron Waksman M.D. et al., "Intracoronary Radiation Before Stent Implantation Inhibits Neointima Formation in Stented Porcine Coronary Arteries", *Circulation*, vol. 92, No. 6, pp. 1383–1386, Sep. 15, 1995.

Christoph Hehrlein, M.D., et al., "Low–Dose Radioactive Endovascular Stents Prevent Smooth Muscle Cell Proliferation and Neointimal Hyperplasia in Rabbits", *Circulation*, vol. 92, No. 6, pp. 1570–1575, Sep. 15, 1995.

–Eric Van't Hooft, et al., "HDR Afterloader for Vascular Use", *Discoveries in Radiation for Restenosis*, Abstract 36, p 113, Jan. 1996.

–Robert E. Fischell, et al., "The Radioisotope Stent: Conception and Implementation", *Discoveries in Radiation for Restenosis*, Abstract 37 , p 115, Jan. 1996.

–Youri Popowski M.D., et al., "Radioactive Wire in a Self–Centering Catheter System", *Discoveries in Radiation for Restenosis*, Abstract 38, pp 117–118, Jan. 1996.

* cited by examiner

STEPPED CENTERING BALLOON FOR OPTIMAL RADIATION DELIVERY

CROSS REFERENCE TO RELATED APPLICATIONS

This application claims the benefit of U.S. Provisional Application No. 60/155,929, filed Sep. 22, 1999.

FIELD OF THE INVENTION

The present invention relates to the field of intravascular radiation therapy. In particular, the present invention relates to catheters used for intravascular delivery of radiation.

DESCRIPTION OF RELATED ART

Coronary artery balloon angioplasty is a minimally invasive technique developed as an alternative to coronary artery bypass grafting for treatment of atherosclerosis, the principle process of heart disease. There are about 450,000 coronary interventions, i.e., angioplasty, atherectomy, and stent, performed annually in the U.S. However, a major limitation of this clinical procedure is the high prevalence of restenosis, or re-narrowing, of the treated vessel. Restenosis occurs approximately 30–50% of the time.

Restenosis occurs as a result of injury to the vessel wall due to the angioplasty procedure, or to other procedures, i.e., stenting, atherectomy, that compress or remove the atherosclerosis and may cause injury to the vessel. Restenosis is a complex process, which can involve immediate vascular recoil, neointimal hyperplasia, and/or late vascular remodeling. Neointimal hyperplasia, a response of the body to balloon-induced physical injury of the vessel wall, is thought to be the main contributor to restenosis. Hyperplasia can result in narrowing of the vessel lumen within 3–6 months after angioplasty due to proliferation of smooth muscle cells in the region injured by the angioplasty. Restenosis can require the patient to undergo repeat angioplasty procedures or by-pass surgery with added costs and risks to the patient.

One method currently used to inhibit restenosis following a procedure such as angioplasty, involves delivery of a prescribed dose of radiation to the walls of the dilated length of vessel through intravascular radiotherapy (IRT). In an example of one method of IRT, a catheter is inserted into a vessel and positioned within the length of vessel dilated by the angioplasty procedure. Once the catheter is positioned, a radiation source is inserted into the lumen of the catheter and positioned to allow delivery of a prescribed dose of radiation to the vessel. Typically the prescribed dose of radiation is delivered at a dose level necessary to inhibit restenosis, and may be termed a therapeutic dose.

Some catheters used in IRT (and some radiation sources where a catheter is not used) may have a smaller diameter than the diameter of the vessel lumen. This differential in diameters provides space for the catheter to move radially as it is positioned within the vessel. If this differential is large enough, a catheter may move and become flexed within the vessel so that the radiation source is not centered within the vessel lumen. In some cases, portions of the catheter may be close to one side of the vessel wall and far from the opposite side and can result in delivery of a non-uniform dose of radiation to the vessel.

FIG. 1 illustrates a longitudinal cross-sectional view of one example of a catheter containing a radiation source inserted within a vessel in the prior art. In the illustration, a catheter 10 is inserted into a vessel 12. The catheter 10 has a longitudinal lumen 14 to receive a radiation source 16. As shown, the catheter 10 has flexed within the vessel during positioning so that portions of the radiation source 16 are not radially centered within the vessel. This positioning can result in the radiation source 16 being closer to the vessel wall at some points (shown at pointer A) and farther from the vessel wall at other points (shown at pointer B).

For a given radiation source, the dose rate drops rapidly as a function of distance from the source axis. Thus, a small change in distance from the source to the surface of the vessel wall can result in a large difference in the radiation dose received by the vessel. If the radiation source 16 is positioned close to the vessel wall, the vessel may receive an overdose of radiation, e.g., a hot spot. Overdosing a vessel wall with radiation can result in vessel damage, such as inflammation, hemorrhaging, and arterial necrosis. Conversely, the side of the vessel wall where the radiation source 16 is positioned away may receive an underdose of radiation so that restenosis may not be inhibited.

In order to mitigate overdosing or underdosing of a vessel, other catheters, such as centering catheters, have been developed to provide more stability in the radial positioning of the radiation source. By positioning the radiation source so that it is substantially centered within the vessel, a more uniform dose of radiation is delivered to the vessel. U.S. Pat. No. 5,643,171 to Bradshaw et al. describes several embodiments of a centering catheter that may be used with IRT. In one embodiment, a centering segment, such as a centering balloon, is attached to the portion of the catheter in which the radiation source is to be located. The balloon can then be inflated so that the radioactive source is substantially centered within the lumen of the vessel.

Recent results from clinical trials and animal studies, however, show a problem in a few of the cases following IRT, in which restenosis occurs at a higher incidence at one or both ends of the treated dilated length of the vessel, as opposed to the middle of the treated length of the vessel. This problem, known as the "edge effect", is common with most current IRT systems, and can subject the patient to the same risks and costs that were initially sought to be avoided by using IRT.

The occurrence of edge effects suggests that an additional length of vessel to each side of the dilated length of vessel may also be injured by stretching and tears to the intima from the angioplasty, or other procedures, and possibly from the radiotherapy catheter. As the radiation source is typically chosen to treat the dilated length, the additional length of injured vessel may not receive a therapeutic dose of radiation.

Further, with some radiation sources used in IRT, the radiation dose delivered at the ends of the radiation source may be less than the dose delivered in the middle. FIG. 2 illustrates the longitudinal dose profile of a radiation source within a centering catheter in the prior art. Typically, a centering catheter 22 is positioned in a vessel so that the centering segment 24 is located within the length of the vessel injured during an intravascular procedure, i.e., the dilated length. For example, if a vessel was dilated with a 27 mm angioplasty balloon, a centering catheter 22 may have a 27 mm centering segment 24 within which a radiation source 26 will be positioned. The dose profile illustrates that if the 27 mm radiation source 26, such as a P32 radiation source, is positioned correctly within the dilated length, the 27 mm radiation source 26 delivers a therapeutic dose of radiation along a length of about 22 mm with a 2–2.5 mm dose fall off at each end. Thus, the radiation source 26 delivers a therapeutic dose of radiation along a length that is shorter than the dilated length of the vessel. This leaves little to no margin for treating additional lengths of injured vessel beyond the dilated length and does not allow room for positioning errors arising from the radiation delivery system or physician.

However, to attempt to treat this additional length of injured vessel by simply using a longer radiation source within the catheter is problematic. Current centering catheters typically do not extend the radiation source beyond the ends of the centering segment, and, typically, do not provide centering for radiation sources that extend beyond the ends of the centering segment. In these catheters, if a radiation source is extended beyond the centering segment in an attempt to treat the additional length of injured vessel, it could potentially damage the vessel by overdosing the vessel wall.

Extending both the length of the centering catheter and the radiation source within it doesn't provide an optimal solution as a longer centering catheter may result in further damage to the vessel compounding the problem. Injury from the centering segment may not be as damaging as the angioplasty balloon but may result in restenosis which is ultimately what the IRT was attempting to avert.

Thus, what is needed is an apparatus that substantially centers a portion of a radiation source within a vessel along a desired treatment length to allow delivery of an approximately uniform dose of radiation and prevents overdosing of the vessel from portions of the radiation source that extend beyond the centered length. Further, the apparatus should mitigate additional injury to the vessel walls outside the centered length.

SUMMARY OF THE INVENTION

The present invention includes a stepped centering catheter for delivery of intravascular radiation therapy that substantially centers a portion of a radioactive source within the lumen of a vessel along a therapeutic treatment length and offsets portions of the radiation source that extend beyond the therapeutic treatment length within a region having a minimum offset from the vessel wall.

BRIEF DESCRIPTION OF THE DRAWINGS

The present invention may best be understood by referring to the following description and accompanying drawings which are used to illustrate embodiments of the invention. In the drawings.

DETAILED DESCRIPTION OF THE INVENTION

The present invention includes a stepped centering catheter which substantially centers a portion of a radiation source within the lumen of a vessel along a therapeutic treatment length and offsets portions of the radiation source that extend beyond the therapeutic treatment length within a region having a minimum offset from the vessel wall.

As earlier discussed, the occurrence of edge effects suggests that an additional length of vessel to each side of a dilated length of vessel may also be injured due to stretching and tears to the intima from the angioplasty and possibly from the radiotherapy catheter or apparatus, and that this additional length of injured tissue may not receive a therapeutic dose of radiation.

In one example of a radiation delivery system, a radiation source may be positioned within a catheter relative to radio-opaque markers so that a therapeutic dose of radiation is delivered along a therapeutic treatment length. The catheter may also substantially center a portion of the radioactive source within the vessel along the therapeutic treatment length so that an approximately uniform dose of radiation is delivered. However, in order to deliver the therapeutic dose within the therapeutic treatment length, portions of the radioactive source may extend beyond the centered therapeutic treatment length. As earlier described, extending the radiation source beyond the centered therapeutic treatment length may result in overdosing the vessel wall. Thus, the present invention may be used to substantially center a portion of the radioactive source within the vessel along the therapeutic treatment length and to mitigate overdosing of the vessel wall by offsetting the portions of the radiation source that extend outside the therapeutic treatment length a minimum distance from the vessel wall.

Figure 1:
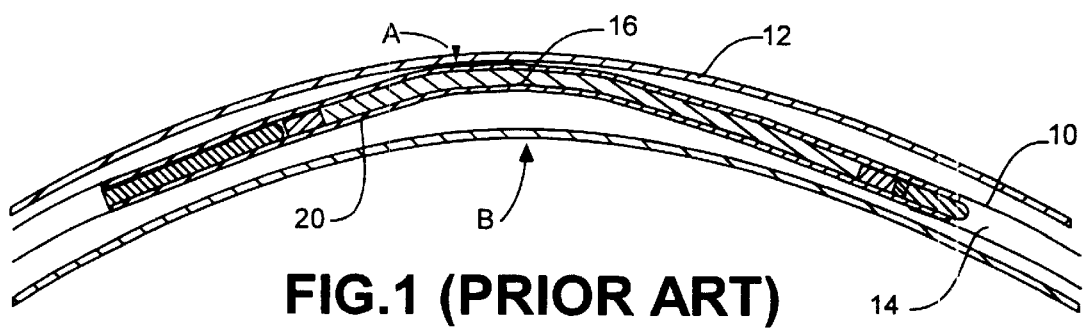
FIG. 1 illustrates a longitudinal cross-sectional view of one example of a catheter containing a radiation source inserted within a vessel in the prior art.
Figure 2:
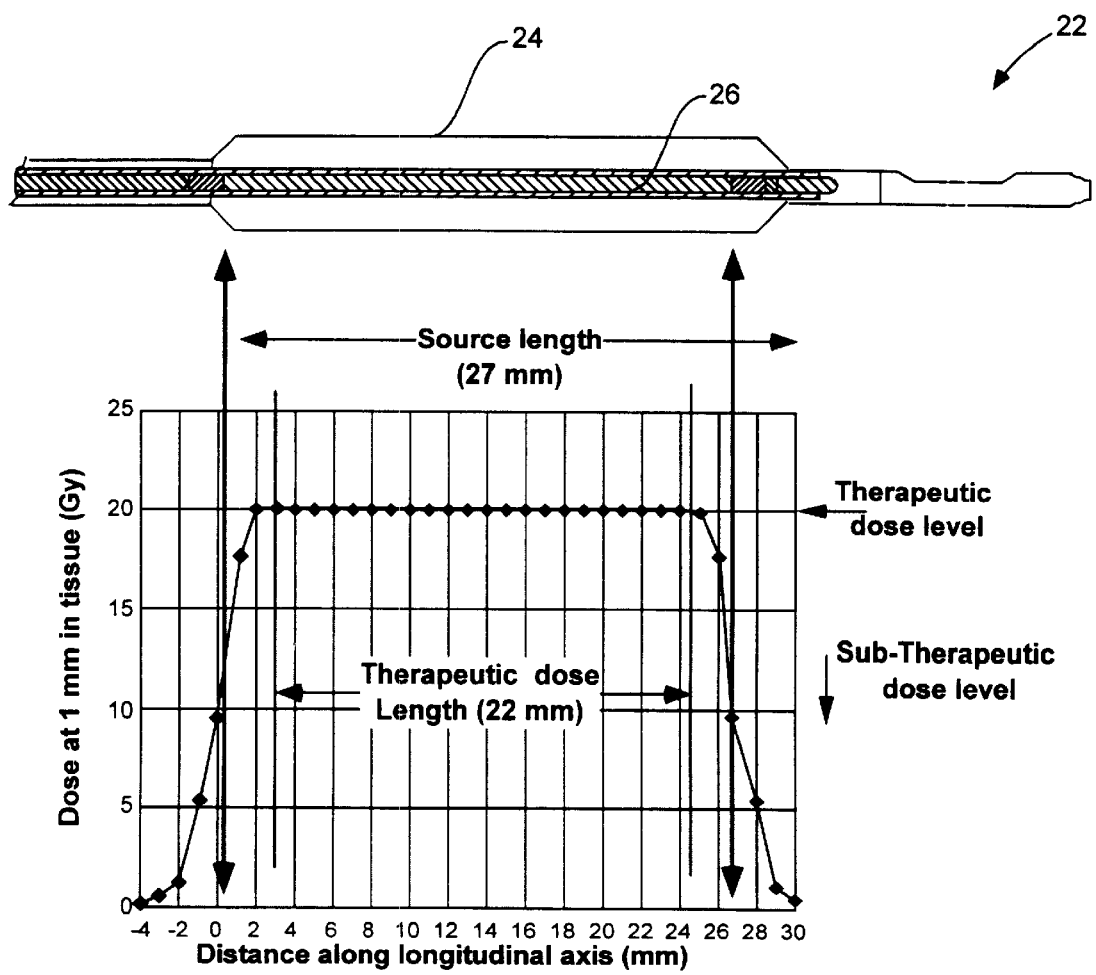
FIG. 2 illustrates the longitudinal dose profile of a radiation source within a centering catheter in the prior art.
Figure 3:
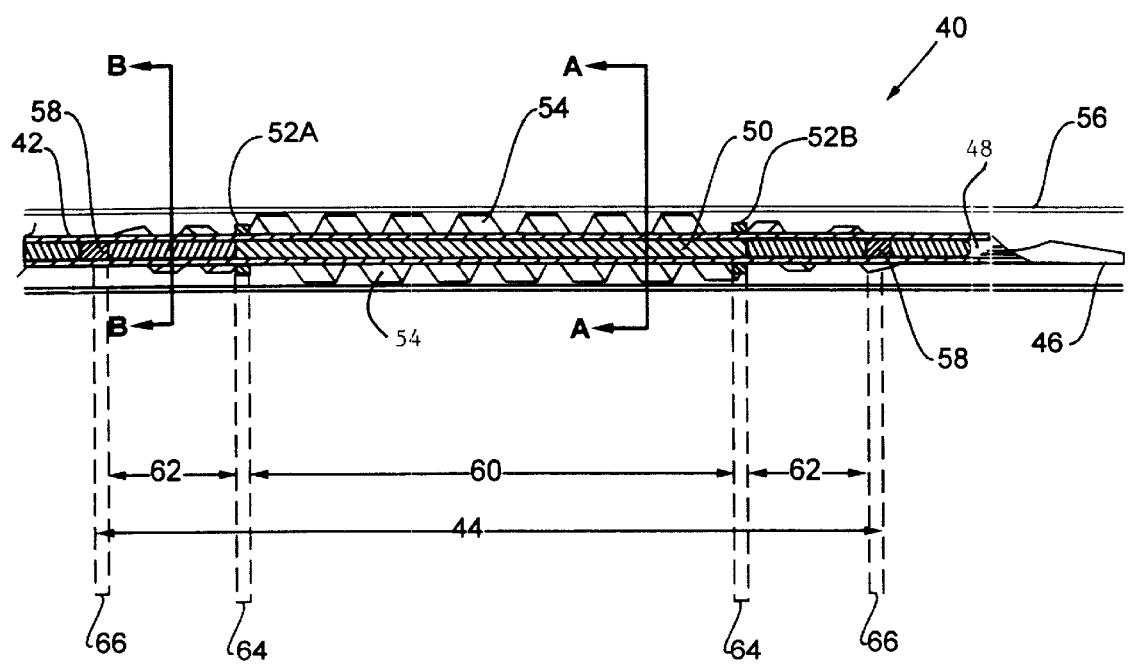
FIG. 3 illustrates a longitudinal cross-sectional view of a stepped centering catheter according to one embodiment of the present invention.

FIG. 3 illustrates a longitudinal cross-sectional view of a stepped centering catheter according to one embodiment of the present invention. In the embodiment of FIG. 3, the stepped centering catheter may be a stepped centering balloon catheter 40 as illustrated. It is to be understood that the present invention may be embodied using structures other than a balloon structure. The stepped centering balloon catheter 40 includes an elongate, tubular shaft 42 and a stepped centering balloon segment 44. The shaft 42 has a proximal end to allow introduction of a radioactive source 50, such as a radioactive source wire, into the shaft lumen 48, and may have an open or closed distal tip 46. The radioactive source 50 may have proximal and distal radio-opaque source markers 58 to enhance visualization by radioimagery systems, such as fluoroscopy. The radio-opaque source markers 58 may be formed of tungsten, or of other materials, such as gold, or platinum.

The proximal end of the stepped centering balloon catheter 40 may be connected to a radiation source delivery device such as an afterloader, or other device, for advancing a radiation source within the stepped centering balloon catheter 40. For example, an afterloader produced by Guidant Corporation, Houston, Tex., may be used. If an afterloader is used in conjunction with the present invention, the stepped centering balloon catheter 40 may be connected to the afterloader system utilizing a key connector that allows the afterloader system to identify the particular characteristics of the stepped centering catheter.

As illustrated in FIG. 3, the stepped centering balloon segment 44 may be formed as a continuous, inflatable helical balloon that forms lobes 54 around the shaft 42. An inflation lumen may be provided at the proximal end of the stepped centering balloon segment 44 to allow inflation from a pump or other inflation apparatus. It is to be understood that the present invention may be embodied by other balloon formations, or by structures other than balloons.

The stepped centering balloon segment 44 may include a central balloon segment 60 of a first diameter and offset balloon segments 62 of a smaller, second diameter. It is to be noted that when inflated, the nature of a helical balloon is such that as the lobes 54 advance and spiral around the length of the shaft 42, an effective diameter is created which limits the radial positioning of the radiation source 50 within the vessel 56.

The stepped centering balloon catheter 40 may have proximal and distal radio-opaque markers 52A and 52B attached to the shaft 42 that delineate the proximal and distal ends of the central balloon segment 60. In this way, the markers 52A and 52B delineate the portion of the radiation source 50 that is substantially centered within the vessel lumen.

In use, the stepped centering balloon catheter 40 is selected so that when properly inflated, the first effective diameter of the central balloon segment 60 is sized to be just large enough to compliantly engage the walls of vessel 56 and to substantially center the shaft lumen 48, and, thus, a portion of the radiation source 50, within the lumen of the vessel 56. For example, the first effective diameter of the central balloon segment 60 may be determined to substantially center a portion of the radiation source 50 which may deliver a therapeutic dose of 20 Gy at 1 mm into the vessel. The first effective diameter of the central balloon segment 60 is stepped down to the smaller, second effective diameter of the offset balloon segments 62 across first steps 64. In this example, the first effective diameter of the central balloon segment 60 is continued to the interior edges of the markers 52A and 52B, i.e., the therapeutic treatment length. Thus, the central balloon segment 60 substantially centers the therapeutic dose region of radiation source 50 between the markers 52A and 52B. The first effective diameter is then gradually tapered to the second effective diameter along the length of the first steps 64.

The second effective diameter of the offset balloon segments 62 is sized to offset portions of the radiation source 50 which extend beyond the central balloon segment 60 within a region having a minimum offset distance from the vessel wall. In this way, the radiation dose delivered to the vessel wall from the portions of the radiation source 50 that extend beyond the central balloon segment 60 may be controlled to prevent overdosing the vessel. For example, the second effective diameter of the offset balloon segments 62 may be determined to limit the radiation dose delivered by the portions of the radiation source 50 which extend beyond the central balloon segment 60, as discussed above, to 100 Gy or less at the vessel surface. Thus, the offset balloon segments 62 offset sub-therapeutic portions of the radiation source 50 that extend outside the markers 52A and 52B to prevent overdosing the vessel. Additionally, although the offset balloon segments 62 may extend beyond the therapeutic treatment length of the vessel, the smaller, second effective diameter should not cause or exacerbate stretches or tears in the vessel, thus mitigating further damage to the vessel.

It is to be noted that although the present embodiment is shown having offset balloon segments 62 both proximal and distal to the central balloon segment 60, in alternative embodiments, the present invention may have only a proximal offset balloon segment 62 or a distal offset balloon segment 62 with the corresponding first and second steps. In these embodiments, the opposite side of the central balloon segment 60 without an offset balloon segment 62 may retain a first step 64 tapering the first effective diameter to the diameter of the shaft 42. In other embodiments, the diameter of the shaft 42 may be sufficiently similar to the first effective diameter so that the opposite side of the central balloon segment 60 without an offset balloon segment 62 may not require a first step 64.

The second effective diameter of the offset balloon segments 62 is stepped down to the smaller diameter of the shaft 42 across second steps 66. In this example, the second effective diameter of the offset balloon segments 62 is continued to the end of the radiation source 50. The second effective diameter is then gradually tapered to the diameter of the shaft 42 along the length of the second steps 66. The first steps 64 and second steps 66 allow for a gradual increase and reduction in the effective diameters created by the helical lobes 54 as the stepped centering balloon catheter 40 is positioned within the vessel. The gradual tapering is provided to allow the vessel walls to gradually respond to the differences in diameters of the centering balloon catheter 40 structure in an attempt to mitigate additional damage to the vessel.

The stepped centering balloon segment 44 may be fabricated using standard techniques well known to those of ordinary skill in the art. In one embodiment, the stepped centering balloon segment 44 may be fabricated using a shape mold and materials of relatively high strength that will expand to a fixed diameter when inflated, such as relatively high strength polymers, i.e., nylon, polyester, or polyvinyl acetate or polyethylene. The stepped centering balloon segment 44 is attached to the shaft 42 by bonds that are located at the ends of the stepped centering balloon segment 44. The bonds may be thermal or ultrasonic welds, adhesive or solvent bonds, or may be formed by other conventional means well known to those of ordinary skill in the art.

The radio-opaque markers 52A and 52B may be gold, platinum, or other materials commonly viewable using radioimagery systems, such as fluoroscopy. The radio-opaque markers 52A and 52B may be attached to the shaft 42 by conventional means well known to those of ordinary skill in the art. In one embodiment, the radio-opaque markers 52A and 52B may be attached to the shaft 42 immediately outside the central balloon segment 60 to delineate the endpoints of the central balloon segment 60. It will be appreciated that when used with the radiation therapy method earlier described, the length of the central balloon segment 60 may be determined according to the therapeutic treatment length calculated for a particular vessel. In this way, using radioimagery systems, the radio-opaque markers 52A and 52B provide a visual landmark of the portion of the radioactive source 50 that is substantially centered within the vessel. It is to be understood that the above techniques and materials are exemplary and not intended to limit the scope of the present invention.

Figure 4:
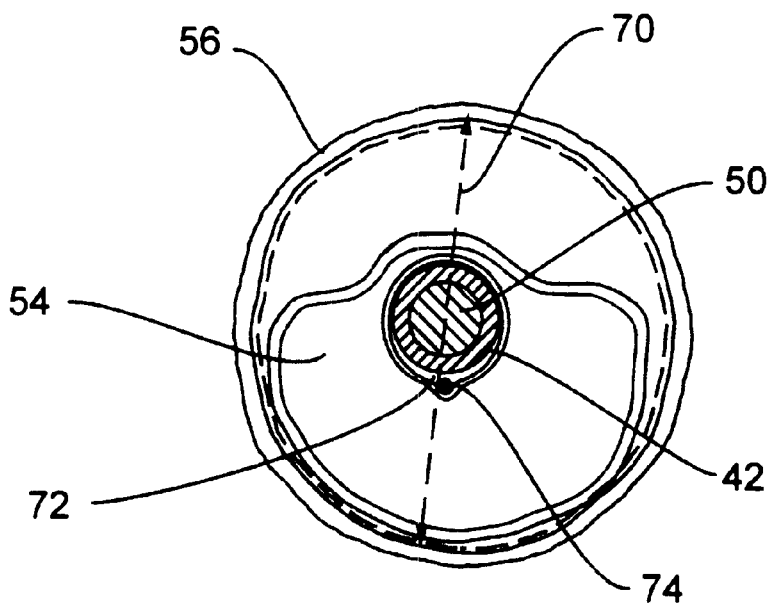
FIG. 4 illustrates a transverse cross-sectional view of the stepped centering catheter of FIG. 3 taken at A—A according to one embodiment of the present invention.

FIG. 4 illustrates a transverse cross-sectional view of the stepped centering catheter of FIG. 3 taken at A—A according to one embodiment of the present invention. In the illustration, the radiation source 50 within the shaft 42 is substantially centered within the lumen of the vessel 56 due to the first effective diameter 70 created by the helical lobes 54 of the central balloon segment 60. This allows for an approximately uniform dose of radiation to be delivered to the vessel wall along the therapeutic treatment length. In the illustration, a support mandrel lumen 72 is shown attached to the shaft 42 to allow insertion of a support mandrel 74. The support mandrel 74 may be introduced proximal to the stepped centering balloon segment 44 and may run substantially the length of stepped centering segment 44 and terminate at the distal tip 46. The support mandrel lumen 72 and support mandrel 74 may be formed and attached to the shaft 42 using methods well known to those of ordinary skill in the art. It is to be understood that other embodiments without a support mandrel lumen 72 and support mandrel 74 may be used and that the inclusion of the structures is not meant to limit the scope of the present invention. Further it is to be understood that the present invention may also be formed with a guidewire lumen for accepting a guidewire, but that the use of a guidewire is not necessary, and is not meant to limit the scope of the present invention.

Figure 5:
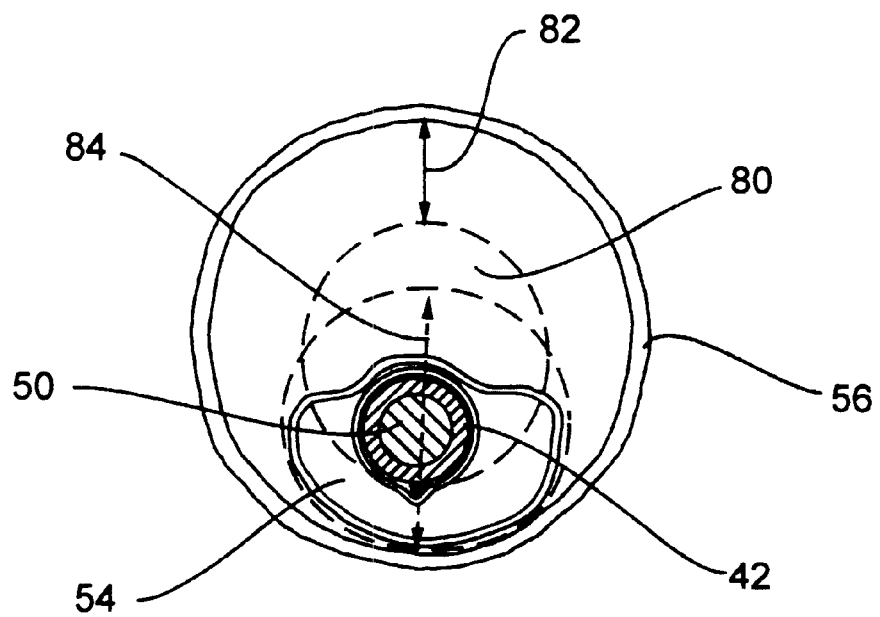
FIG. 5 illustrates a transverse cross-sectional view of the stepped centering catheter of FIG. 3 taken at B—B according to one embodiment of the present invention.

FIG. 5 illustrates a transverse cross-sectional view of the stepped centering catheter of FIG. 3 taken at B—B according to one embodiment of the present invention. In this embodiment, the radiation source 50 is located within the shaft 42 and is maintained within a region 80 having a minimum offset distance 82 from the vessel wall. The minimum offset distance 82 is provided by the smaller, second effective diameter 84 created by the helical lobes 54 in the offset balloon segments 62. Thus, although the portions of the radiation source 50 in the offset balloon segments 62 have more area of movement within the vessel 56 than the portion of the radiation source 50 within the central balloon segment 60, they are constrained to the region 80. The region 80 is maintained at the offset distance 82 so that the radiation dose delivered to the vessel wall is equal to or less than a dosage determined by the minimum offset distance 82. For example, the second effective diameter 84 may be determined to provide a minimum offset distance 82 from the vessel wall so that the radiation dose delivered to the vessel is 100 Gy or less at the vessel surface. Depending upon the radiation source, and the desired maximum radiation dose, the offset distance 82 may be varied by varying the second effective diameter 84. In this way, the offset balloon segments 62 mitigate overdosing of the vessel by portions of the radiation source 50 that extend beyond the therapeutic treatment length.

Figure 6:
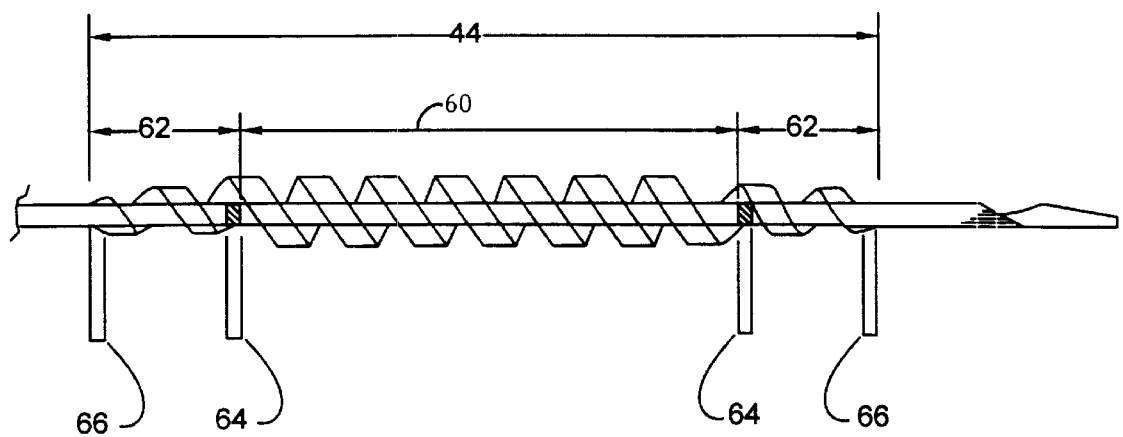
FIG. 6 illustrates an external side view of the stepped centering catheter of FIG. 3 according to one embodiment of the present invention.

FIG. 6 illustrates an external side view of the stepped centering balloon catheter of FIG. 3 according to one embodiment of the present invention. In this embodiment, the stepped centering balloon segment 44 may have a 32 mm length central balloon segment 60, 1 mm length first steps 64, 5 mm length offset balloon segments 62, and 1 mm length second steps 66.

In another embodiment, the stepped centering balloon segment 44 may have a 52 mm length central balloon segment 60, 1 mm length first steps 64, 5 mm length offset balloon segments 62, and 1 mm length second steps 66.

It is to be understood that the above embodiments are only exemplary, and that other lengths may be used as necessitated by the length of the vessel to be treated and by the length of the portion of the radiation source that is to be radially centered as well as the length of the portion to be offset. For example, in coronary applications, the length of the central balloon segment 60 may range from 12 mm to 90 mm. The length of the offset balloon segments 62 may range from 2 mm to 10 mm. In peripheral applications, the length of the central balloon segment 60 may range from 5 cm to 20 cm. The length of the offset balloon segments 62 may range from 2 mm to 15 mm. However, the above ranges are only exemplary and the lengths will depend on the design of the radiation system and specific isotope used.

To enable utilization of the present invention within vessels of different diameters the above-described embodiments of the present invention may be formed with a variety of first and second diameters (including effective diameters). The first and second diameters should be selected so that in combination the first diameter substantially centers a portion of the radiation source within the lumen of the vessel along the therapeutic treatment length and the second diameter offsets portions of the radiation source that extend beyond the central balloon segment 60 a minimum distance from the vessel wall. Additionally the minimum offset distance should be determined at a distance which mitigates overdosing a vessel. For example, in the following embodiments the second diameter may be selected to provide a minimum offset distance 82 of a $^{32}$P radiation source from the vessel so that the radiation dose is 100 Gy or less at the surface of the vessel.

In one embodiment, when inflated, the central balloon segment 60 may have a 2.5 mm outer effective first diameter 70 and the offset balloon segments 62 may have 1.75 mm outer effective second diameters 84.

In a second embodiment, when inflated, the central balloon segment 60 may have a 3.0 mm outer effective first diameter 70 and the offset balloon segments 62 may have 2.0 mm outer effective second diameters 84.

In a third embodiment, when inflated, the central balloon segment 60 may have a 3.5 mm outer effective first diameter 70 and the offset balloon segments 62 may have 2.25 mm outer effective second diameters 84.

In a fourth embodiment, when inflated, the central balloon segment 60 may have a 4.0 mm outer effective first diameter 70 and the offset balloon segments 62 may have 2.5 mm outer effective second diameters 84.

It is to be understood that the above embodiments are exemplary and that other diameters may be used. For example, in coronary applications the outer effective first diameter 70 may range in size from 2.0 mm to 4.0 mm. The outer effective second diameters 84 may range from 1.5 mm to 3.0 mm. In peripheral applications, the outer effective first diameter 70 may range in size from 4.0 mm to 10 mm. The outer effective second diameters 84 may range from 2.0 mm to 7.0 mm. The above ranges are only exemplary and other diameters may be used dependent in large part upon the isotope selected.

Figure 7:
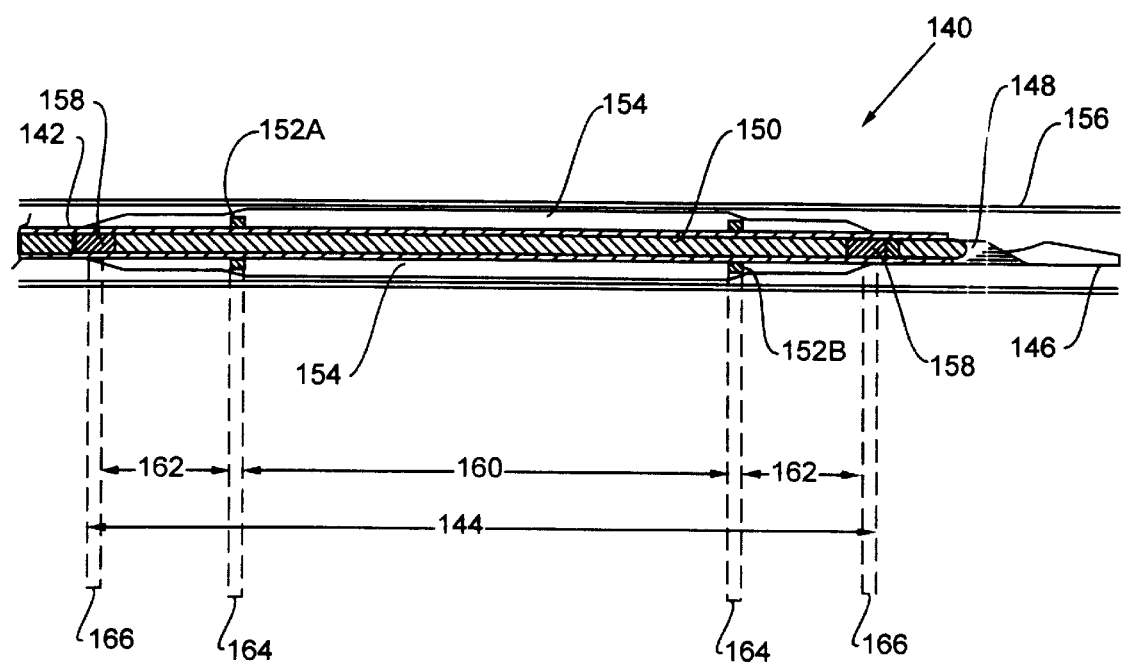
FIG. 7 illustrates a longitudinal cross-sectional view of a stepped centering catheter according to another embodiment of the present invention.

FIG. 7 illustrates a longitudinal cross-sectional view of a stepped centering catheter according to another embodiment of the present invention. In the embodiment of FIG. 7, the stepped centering catheter may be a stepped centering fluted balloon catheter 140 as illustrated. It is to be understood that the present invention may be embodied using structures other than a fluted balloon structure. The stepped centering fluted balloon catheter 140 includes an elongate, tubular shaft 142 and a stepped centering fluted balloon segment 144. The shaft 142 has a proximal end to allow introduction of a radioactive source 150, such as a radioactive source wire, into the shaft lumen 148, and may have an open or closed distal tip 146. The radioactive source 150 may have proximal and distal radio-opaque source markers 158 to enhance visualization by radioimagery systems, such as fluoroscopy. The radio-opaque source markers 158 may be formed of tungsten, or of other materials, such as gold, or platinum.

The proximal end of the stepped centering fluted balloon catheter 140 may be connected to a radiation source delivery device such as an afterloader, or other device, for advancing a radiation source within the stepped centering fluted balloon catheter 140. For example, an afterloader produced by Guidant Corporation, Houston, Tex., may be used. If an afterloader is used in conjunction with the present invention, the stepped centering fluted balloon catheter 140 may be connected to the afterloader system utilizing a key connector that allows the afterloader system to identify the particular characteristics of the stepped centering catheter.

As illustrated in FIG. 7, the stepped centering fluted balloon segment 144 may be formed as a continuous, inflatable fluted balloon including a plurality of individual fluted lobes 154 spaced around the shaft 142. An inflation lumen may be provided at the proximal end of the stepped centering fluted balloon segment 144 to allow inflation from a pump or other inflation apparatus. It is to be understood that the present invention may be embodied by other balloon formations, or by structures other than fluted balloons.

The stepped centering fluted balloon segment 144 may include a central fluted balloon segment 160 of a first diameter and offset fluted balloon segments 162 of a smaller, second diameter. It is to be noted that when inflated, the nature of a fluted balloon is such that together the individual fluted lobes 154 create an effective diameter which limits the radial positioning of the radiation source 150 within the vessel 156.

The stepped centering fluted balloon catheter 140 may have proximal and distal radio-opaque markers 152A and 152B attached to the shaft 142 that delineate the proximal and distal ends of the central fluted balloon segment 160. In this way, the markers 152A and 152B delineate the portion of the radiation source 150 that is substantially centered within the vessel lumen.

Figure 7A:
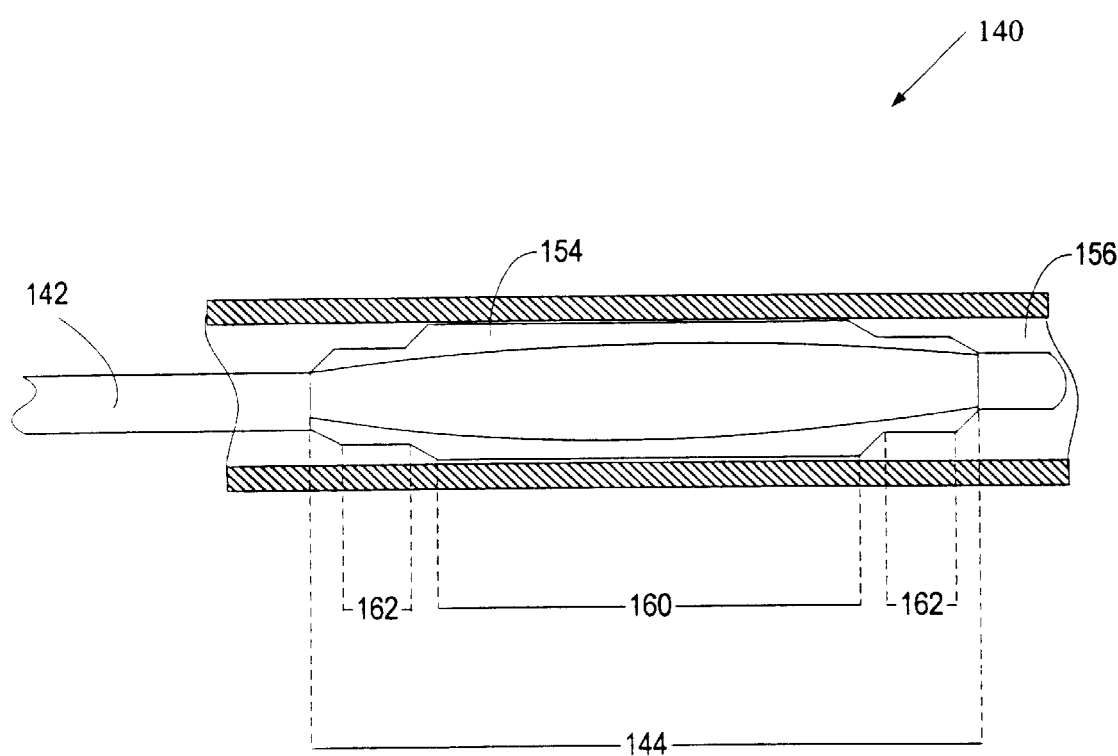
FIG. 7A illustrates a longitudinal side view of a stepped centering catheter of FIG. 7.

FIG. 7A illustrates a perspective view of the stepped centering fluted balloon 140 around shaft 142, as illustrated in FIG. 7. The stepped centering balloon segment 144 may include a central fluted balloon segment 160 of a first diameter and offset fluted balloon segments 162 of a smaller, second diameter. The individual fluted lobes 154, illustrated as inflated within vessel 156, create an effective diameter that limits the radial positioning of a radiation source (e.g., radiation source 150).

In use, the stepped centering fluted balloon catheter 140 is selected so that when properly inflated, the first effective diameter of the central fluted balloon segment 160 is sized to be just large enough to compliantly engage the walls of vessel 156 and to substantially center the shaft lumen 148, and, thus, a portion of the radiation source 150, within the lumen of the vessel 156. For example, the first effective diameter of the central fluted balloon segment 160 may be determined to substantially center a portion of the radiation source 150 which may deliver a therapeutic dose of 20 Gy at 1 mm into the vessel. The first effective diameter of the central fluted balloon segment 160 is stepped down to the smaller, second effective diameter of the offset fluted balloon segments 162 across first steps 164. In this example, the first effective diameter of the central fluted balloon segment 160 is continued to the interior edges of the markers 152A and 152B, i.e., the therapeutic treatment length. Thus, the central fluted balloon segment 160 substantially centers the therapeutic dose region of radiation source 150 between the markers 152A and 152B. The first effective diameter is then gradually tapered to the second effective diameter along the length of the first steps 164.

The second effective diameter of the offset fluted balloon segments 162 is sized to offset portions of the radiation source 150 which extend beyond the central fluted balloon segment 160 within a region having a minimum offset distance from the vessel wall. In this way, the radiation dose delivered to the vessel wall from the portions of the radiation source 150 that extend beyond the central fluted balloon segment 160 may be controlled to prevent overdosing the vessel. For example, the second effective diameters of the offset fluted balloon segments 162 may be determined to limit the radiation dose delivered by the portions of the radiation source 150 which extend beyond the central fluted balloon segment 160, as discussed above, to 100 Gy or less at the vessel surface. Thus, the offset fluted balloon segments 162 offset sub-therapeutic portions of the radiation source 150 that extend outside the markers 152A and 152B to prevent overdosing the vessel. Additionally, although the offset fluted balloon segments 162 may extend beyond the therapeutic treatment length of the vessel, the smaller, second effective diameter should not cause or exacerbate stretches or tears in the vessel, thus mitigating further damage to the vessel.

It is to be noted that although the present embodiment is shown having offset fluted balloon segments 162 both proximal and distal to the central fluted balloon segment 160, in alternative embodiments, the present invention may have only a proximal offset fluted balloon segment 162 or a distal offset fluted balloon segment 162 with the corresponding first and second steps. In these embodiments, the opposite side of the central fluted balloon segment 160 without an offset fluted balloon segment 162 may retain a first step 164 tapering the first effective diameter to the diameter of the shaft 142. In other embodiments, the diameter of the shaft 142 may be sufficiently similar to the first effective diameter so that the opposite side of the central fluted balloon segment 160 without an offset fluted balloon segment 162 may not require a first step 164.

The second effective diameter of the offset fluted balloon segments 162 is stepped down to the smaller diameter of the shaft 142 across second steps 166. In this example, the second effective diameter of the offset fluted balloon segments 162 is continued to the end of the radiation source 150. The second effective diameter is then gradually tapered to the diameter of the shaft 142 along the length of the second steps 166. The first steps 164 and second steps 166 allow for a gradual increase and reduction in the effective diameters created by the fluted lobes 154 as the stepped centering fluted balloon catheter 140 is positioned within the vessel. The gradual tapering is provided to allow the vessel walls to gradually respond to the differences in diameters of the centering fluted balloon catheter 140 structure in an attempt to mitigate additional damage to the vessel.

The stepped centering fluted balloon segment 144 may be fabricated using standard techniques well known to those of ordinary skill in the art. In one embodiment, the stepped centering fluted balloon segment 144 may be fabricated using a shape mold and materials of relatively high strength that will expand to a fixed diameter when inflated, such as relatively high strength polymers, i.e., nylon, polyester, or polyvinyl acetate or polyethylene. The stepped centering fluted balloon segment 144 is attached to the shaft 142 by bonds that are located at the ends of the stepped centering fluted balloon segment 144. The bonds may be thermal or ultrasonic welds, adhesive or solvent bonds, or may be formed by other conventional means well known to those of ordinary skill in the art.

The radio-opaque markers 152A and 152B may be gold, platinum, or other materials commonly viewable using radioimagery systems, such as fluoroscopy. The radio-opaque markers 152A and 152B may be attached to the shaft 142 by conventional means well known to those of ordinary skill in the art. In one embodiment, the radio-opaque markers 152A and 152B may be attached to the shaft 142 immediately outside the central fluted balloon segment 160 to delineate the endpoints of the central fluted balloon segment 160. It will be appreciated that when used with the radiation therapy method earlier described, the length of the central fluted balloon segment 160 may be determined according to the therapeutic treatment length calculated for a particular vessel. In this way, using radioimagery systems, the radio-opaque markers 152A and 152B provide a visual landmark of the portion of the radioactive source 150 that is substantially centered within the vessel. It is to be understood that the above techniques and materials are exemplary and not intended to limit the scope of the present invention.

Thus, there has been described several embodiments of a stepped centering catheter according to the present invention for delivery of intravascular radiation therapy in which a portion of a radiation source is substantially centered within the lumen of a vessel along a therapeutic treatment length and portions of the radiation source that extend outside the therapeutic treatment length are constrained within a region that has a minimum offset from the vessel wall.

In one embodiment, the present invention provides a stepped centering balloon catheter with a stepped centering balloon segment including a central balloon segment of a first effective diameter continuous with smaller offset balloon segments of a second effective diameter located to each side of the central balloon segment. The first effective diameter of the central balloon segment is reduced to the smaller, second effective diameters of the offset balloon segments across first steps, and the second effective diameters of the offset balloon segments are reduced to the shaft diameter of the catheter across second steps.

The first effective diameter substantially centers a portion of a radiation source within a vessel so that a therapeutic dose of radiation may be delivered along a therapeutic treatment length. The second effective diameter constrains portions of a radiation source that extends outside the therapeutic treatment length within a region having a minimum offset from the vessel wall. The first and second steps provide a tapered transition between the different balloon segment diameters and the shaft diameter to mitigate further damage to vessel outside the therapeutic treatment length.

In alternative embodiments, a single offset balloon adjacent to either the proximal or distal end of the central balloon segment may be utilized. In these alternative embodiments, the first effective diameter of the central balloon segment is reduced to the effective diameter of the offset balloon segment across a first step, and the second effective diameter of the offset balloon segment is reduced to the shaft diameter across a second step. The opposite side of the central balloon segment may either be reduced to the shaft diameter across a first step, or may not require a reduction due to the size of the shaft diameter.

It is to be understood that the radio-opaque markers and marker materials discussed with reference to the above examples are merely for illustration, and that other markers, fewer or no markers, and other marker materials may be used. It is to be further understood that when radio-opaque markers are discussed herein, the markers may be other than radio-opaque if viewable using a radioimagery system. Additionally, although the present invention was discussed with reference to a $^{32}P$ radiation source, it is to be understood that radiation sources other than $^{32}P$ may be used with this invention and that modification of the first and second diameters and minimum offset distances may be required. For example, radiation sources may utilize different isotopes and geometries in addition to those described herein.

In the foregoing specification, the invention has been described with reference to specific exemplary embodiments thereof. It will, however, be evident that various modifications and changes may be made thereto without departing from the broader spirit and scope of the invention as set forth in the appended claims. In particular, structures other than a balloon, or a helical or fluted balloon, may also be used. The specification and drawings are, accordingly, to be regarded in an illustrative rather than a restrictive sense.

We claim:

1. A catheter for delivery of intravascular radiation therapy comprising:
   an elongate, tubular shaft, said shaft having a shaft diameter, and a lumen for receiving a radiation source; and
   a balloon having a stepped centering segment attached to said elongate, tubular shaft, said stepped centering segment further comprising:
      a central segment, said central segment having a first diameter and proximal and distal ends;
      first step segments adjacent to each of said proximal and distal ends of said central segment;
      offset segments adjacent to each of said first step segments, said offset segments having a second diameter; and
      second step segments adjacent to each said offset segments and having a third diameter that is less than said second diameter.

2. The catheter of claim 1 wherein said first diameter substantially centers a portion of said radiation source within the lumen of a vessel.

3. The catheter of claim 2 wherein said second diameter is less than said first diameter and offsets portions of said radiation source which extend outside said central segment at least a minimum offset distance from the walls of said vessel.

4. The catheter of claim 3 wherein said first diameter is reduced to said second diameter across said first steps.

5. The catheter of claim 4 wherein said second diameter is reduced to said shaft diameter across said second steps.

6. The catheter of claim 1 wherein said stepped centering segment of said balloon comprises an inflatable helical balloon.

7. The catheter of claim 1 further including proximal and distal radio-opaque markers which delineate the proximal and distal ends of the central segment.

8. A stepped centering balloon catheter for delivery of intravascular radiation therapy comprising:
   a tubular, elongate shaft, said shaft having a lumen for receiving a radiation source; and
   a centering balloon segment attached to said tubular, elongate shaft, said centering balloon segment further comprising:
      a central balloon segment, said central balloon segment having a first diameter and proximal and distal ends;
      first balloon step segments adjacent to and continuous with each of said proximal and distal ends of said central balloon segment;
      offset balloon segments, adjacent to and continuous with each of said first balloon step segments, said offset balloon segments having a second diameter; and
      second balloon step segments adjacent to and continuous with each of said offset balloon segments and having a third diameter that is less than said second diameter.

9. The stepped centering balloon catheter of claim 8 wherein said first diameter substantially centers said radiation source within the lumen of a vessel.

10. The stepped centering balloon catheter of claim 9 wherein said second diameter is less than said first diameter and offsets said radiation source within a region having a minimum offset from the walls of said vessel.

11. The stepped centering balloon catheter of claim 10 wherein said first diameter is reduced to said second diameter across said first step.

12. The stepped centering balloon catheter of claim 11 wherein said second diameter is reduced to said shaft diameter across said second step.

13. The stepped centering balloon catheter of claim 12 wherein said centering balloon segment further comprises helical lobes and said first and second diameters are effective diameters.

14. The stepped centering balloon catheter of claim 13 further including proximal and distal radio-opaque markers attached to said shaft that delineate the proximal and distal ends of the central balloon segment.

15. The stepped centering balloon catheter of claim 12 wherein said centering balloon segment further comprises a plurality of fluted lobes and said first and second diameters are effective diameters.

16. The stepped centering balloon catheter of claim 15 further including proximal and distal radio-opaque markers attached to said shaft that delineate the proximal and distal ends of the central balloon segment.

17. A catheter for delivery of intravascular radiation therapy comprising:
an elongate, tubular shaft, said shaft having a shaft diameter, and a lumen for receiving a radiation source; and
a balloon having a stepped centering segment attached to said elongate, tubular shaft, said stepped centering segment further comprising:
a central segment, said central segment having a first diameter and proximal and distal ends;
at least one first step segment adjacent to one of said proximal and distal ends of said central segment;
at least one offset segment adjacent to said at least one first step segment, said at least one offset segment having a second diameter; and
at least one second step segment adjacent to said at least one offset segment and having a third diameter that is less than said second diameter.

18. The catheter of claim 17 wherein said first diameter substantially centers a portion of said radiation source within the lumen of a vessel.

19. The catheter of claim 18 wherein said second diameter is less than said first diameter and offsets a portion of said radiation source which extends outside said central segment at least a minimum offset distance from the wall of said vessel.

20. The catheter of claim 19 wherein said first diameter is reduced to said second diameter across said first step.

21. The catheter of claim 20 wherein said second diameter is reduced to said shaft diameter across said second step.

22. The catheter of claim 21 wherein said stepped centering segment of said balloon comprises an inflatable helical balloon.

23. The catheter of claim 21 wherein said stepped centering segment is an inflatable fluted balloon.

24. The catheter of claim 21 further including proximal and distal radio-opaque markers which delineate the proximal and distal ends of the central segment.

25. The catheter of claim 21 wherein said at least one offset segment is located adjacent to said proximal end of said central segment.

26. The catheter of claim 21 wherein said at least one offset segment is located adjacent to said distal end of said central segment.

27. A method for delivery of intravascular radiation therapy to an injured length of vessel comprising:
substantially centering said injured length of vessel between a proximal and a distal marker on a stepped centering catheter, said proximal and distal markers defining a treatment length, said stepped centering catheter further comprising:
an elongate, tubular shaft, said shaft having a shaft diameter, and a lumen for receiving a radiation source; and
a balloon having a stepped centering segment attached to said elongate, tubular shaft, said stepped centering segment further comprising:
a central segment, said central segment having a first diameter and proximal and distal ends, wherein said central segment substantially radially centers portions of said radiation source between said proximal and distal markers within the vessel lumen;
first step segments adjacent to and continuous with each of said proximal and distal ends of said central segment, wherein said first step segments reduce said first diameter to the second diameters of offset segments;
offset segments adjacent to and continuous with said first step segments, said offset segments having a second diameter, wherein said second diameters offset portions of said radiation source that extend outside said proximal and distal markers a minimum distance from the vessel wall; and
second step segments adjacent to and continuous with said offset segments, wherein said second step segments reduce said second diameter to said shaft diameter.

28. The method of claim 27 further comprising inserting a radiation source within said lumen of said shaft, and delivering a prescribed dose of radiation to said vessel.

29. The method of claim 28 wherein said stepped centering segment of said balloon comprises a stepped centering balloon.

30. The method of claim 29 wherein said balloon is a helical balloon.

31. The method of claim 29 wherein said balloon is a fluted balloon.

32. The method of claim 27 wherein said treatment length is a therapeutic treatment length.

* * * * *